United States Patent
Saido et al.

(10) Patent No.: US 7,122,374 B1
(45) Date of Patent: Oct. 17, 2006

(54) AMYLOID BETA-PROTEIN 3(PE)-42 ANTIBODIES AND USES THEREOF

(76) Inventors: Takaomi Saido, Laboratory for Proteolytic Neuroscience RIKEN Brain Science Institute 2-1 Hirosawa, Wako-shi, Saitama 351-0198 (JP); Takashi Kuda, 41-8, Takada 3-chome, Toshima-ku, Tokyo 171-0033 (JP)

( * ) Notice: Subject to any disclaimer, the term of this patent is extended or adjusted under 35 U.S.C. 154(b) by 246 days.

(21) Appl. No.: 10/406,980

(22) Filed: Apr. 4, 2003

Related U.S. Application Data

(60) Provisional application No. 60/371,205, filed on Apr. 9, 2002.

(51) Int. Cl.
  *C12N 5/20* (2006.01)
  *C07K 16/18* (2006.01)
  *C12P 21/08* (2006.01)
  *A61K 39/395* (2006.01)

(52) U.S. Cl. .................. 435/331; 435/346; 530/388.1; 530/387.3; 424/141.1; 424/133.1; 424/134.1; 424/135.1; 424/139.1

(58) Field of Classification Search ............... None
See application file for complete search history.

(56) References Cited

U.S. PATENT DOCUMENTS 5,750,349 A * 5/1998 Suzuki et al. ............ 435/7.1

OTHER PUBLICATIONS

Harlow E, Lane D. Antibodies: A Laboratory Manual. Cold Spring Harbor Laboratory, New York, 1988, pp. 141-142, 287, 500-501.*

Saido TC et al. Dominant and differential deposition of distinct beta-amyloid peptide species, AbetaN3(pE), in senile plaques, Neuron, Feb. 1995, 14:457-466.*

Harigaya et al., 2000, "Amyloid β Protein Starting Pyroglutamate at Position 3 . . . " *Biochem. Biophys. Res. Commun.* 276:422-427.

*Kamiya Biomedical Company* product data sheet for β-Amyloid (1-42) peptide (May 5, 2001).

Pardridge, "Targeting Protein Therapeutics and Gene . . . ", 2001, Seitai no Kagaku, vol. 52(6):577-83.

Temsamani et al., "Brain drug delivery technologies: . . . ", 2000, Pharm. Sci. & Tech. Today, vol. 3(5):155-62.

Rousselle et al., "New Advances in the Transport of . . . ", 2000, Mol. Pharmacol., vol. 57(4):679-86.

Saido, 1997, Shinkei-Shinpo, vol. 41(1): 58-69 (English abstract on p. 69).

Synt-em pamphlet, "A closer look at Pep:trans", 2001.

Kaneko I et al., 2000, Molecular Medicine, vol. 37(9);1030-42, along with 2-page concise English language explanation of reference.

* cited by examiner

*Primary Examiner*—Janet L. Andres
*Assistant Examiner*—Kimberly A. Ballard
(74) *Attorney, Agent, or Firm*—Fish & Richardson P.C.

(57) ABSTRACT

$A\beta_{N3pE-42}$ is a β amyloid protein that accumulates specifically as a major constituent of senile plaque in the brains of both sporadic and familial Alzheimer's disease patients. The invention provides antibodies that specifically recognize $A\beta_{N3pE-42}$ and can be expected to have a strong β amyloid-removing action. Particularly, humanized antibodies against $A\beta_{N3pE-42}$ are useful to treat human neurodegenerative diseases. Further, since $A\beta_{N3pE-42}$ is localized in the brain, the antibodies of the invention can avoid side effects such as kidney disorders caused by the formation of antigen-antibody complex in the blood. An agent for gene therapy using a vector in which a cDNA encoding a protein comprises the antigen-binding region of the antibody can be an efficient therapeutic drug for removing β amyloid from the brain.

7 Claims, No Drawings

AMYLOID BETA-PROTEIN 3(PE)-42 ANTIBODIES AND USES THEREOF

RELATED APPLICATIONS

This application claims the benefit of Provisional Application Ser. No. 60/371,205, filed Apr. 9, 2002, the contents of which are incorporated herein by reference in their entirety.

TECHNICAL FIELD

The present invention relates to therapeutic methods and agents for diseases related to amyloid β protein.

BACKGROUND OF THE INVENTION

One of the hallmarks of Alzheimer's disease (AD) or senile dementia of Alzheimer type (characterized by the disturbance of memory) is the presence of characteristic lesions called senile plaques, which are observed from the earliest stage of the disease in the brains of Alzheimer patients. Senile plaques contain aggregates of amyloid β protein (amyloid beta-protein; Aβ) a protein having a 40-amino acid and a 42-amino acid form. The formation and accumulation of senile plaques is highly specific to Alzheimer's disease and precedes the neurofibrillary degeneration that is also characteristic of the disease. Thus, the plaques are assumed to be a leading cause of Alzheimer's disease. The accumulation of Aβ has also been observed in the brains of patients with Down's syndrome. Thus, the accumulation of Aβ has also been believed to be a major cause of the neurological symptoms of Down's syndrome. Because of this, suppressing the accumulation of Aβ has become of major interest as a therapeutic strategy for neurodegenerative diseases.

A recent report describes a method for suppressing the accumulation of Aβ using Aβ vaccination in a mouse model (Schenk et al., Nature 400:173–177, 1999). In this study, the authors aim at preventing the deposition of Aβ in the brain by inducing, via vaccination, a host immune response to Aβ.

In another report, transgenic mice overexpressing a gene encoding a mutated amyloid precursor protein (APP) showed deposition of Aβ in the brain with aging. However, immunization of the mice with $A\beta_{1-42}$ at an early age (before the onset of Alzheimer-type neuropathologies) induced the production of antibodies against Aβ and prevented the development of Aβ-plaque formation. Immunization of older mice markedly decreased Aβ deposition in the brain and reduced the extent and progression of AD-like neuropathologies (Schenk et al., Nature 400:173–177, 1999). This suggests the possibility that antibodies produced in the body bind to Aβ and inhibit the formation of amyloid aggregates. The hypothesis is supported by the documented result that the direct peripheral administration of an anti-Aβ antibody also suppressed Aβ deposition in the brain (Bard et al., Nature Med. 6:916–919, 2000).

In addition, other reports describe the anti-AD effect of Aβ vaccines. For example, the inoculation of Aβ not only reduced the deposition of Aβ protein but also improved the impaired learning ability of APP mutant mice with aging (Janus et al., Nature 408:979–982, 2000; Morgan et al., Nature 408:982–985, 2000).

These findings provide supporting evidence for the idea that immunotherapy using Aβ protein as a target is useful as a method for treating AD and the like. However, Aβ protein is present in the serum as well as in AD brain lesions. Accordingly, an anti-Aβ antibody administered to a patient may react to Aβ protein in serum, forming immune complexes. Such immune complexes may potentially lead to kidney disorders. In other words, kidney disorders may be potential side effects of immunotherapy using Aβ protein as a target.

There are two types of Aβ proteins, $A\beta_{42}$ and $A\beta_{40}$. $A\beta_{42}$ is a 42-amino acid protein whose sequence is DAEFRHDSGYEVHHQKLVFFAEDVGSNKGAIIGLMVGGVVIA (SEQ ID NO:1). $A\beta_{40}$ is a truncated Aβ protein lacking the last two amino acid residues of $A\beta_{42}$ at the C-terminal end. Truncation is achieved by digestion with secretase γ. $A\beta_{42}$ is inclined to aggregate more easily than $A\beta_{40}$. Thus, $A\beta_{42}$ is assumed to play an important role in the accumulation of Aβ.

$A\beta_{N3pE-42}$ is a particular species of $A\beta_{42}$ which lacks the first two amino acid residues at the N-terminus of $A\beta_{42}$ and has a pyroglutamate which has been converted from the glutamic acid (E) at the third amino acid position. $A\beta_{N3pE-42}$ is a major protein constituent of senile plaque, and accumulates from early stages of Down's syndrome and Alzheimer's disease (Saido et al., Neuron 14: 457–466, 1995; Harigaya et al. Biochem. Biophys. Res. Com. 276: 422–427, 2000). A glutamic acid (E) is pyroglutamylated to a pyroglutamate residue (pyroglutamyl formation). Recent studies have showed that $A\beta_{N3pE-42}$ comprises nearly 50% of Aβ protein accumulating in brain tissues. The amino acid sequence containing a pyroglutamylated glutamic acid residue at the third amino acid position exhibits a longer half-life in the brain. Thus, the protein containing the pyroglutamylated amino acid is presumed to remain in the brain for a long period. These facts indicate that ensuring the removal of $A\beta_{N3pE-42}$ is a therapeutically important challenge.

SUMMARY OF THE INVENTION

An objective of the present invention is to provide antibodies and immunotherapy for the treatment of diseases, e.g., neurodegenerative diseases, characterized by aberrant accumulation of Aβ. More specifically, the objective of the present invention is to provide antibodies that specifically recognize $A\beta_{N3pE-42}$ and to target $A\beta_{N3pE-42}$ in immunotherapy. An antibody of the invention can be a monoclonal antibody or antigen binding fragment thereof, a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like. An antibody that specifically recognizes $A\beta_{N3pE-42}$ is an antibody that binds to $A\beta_{N3pE-42}$ with a substantially higher affinity than to $A\beta_{42}$ or $A\beta_{40}$. A preferred antibody reacts with $A\beta_{N3pE-42}$ but does not substantially react with $A\beta_{42}$ or $A\beta_{40}$.

Another objective of the present invention is to provide a vaccine capable of inducing the production of antibodies that specifically recognize $A\beta_{N3pE-42}$ in the hosts.

Further, yet another objective of the present invention is to provide pharmaceutical compositions comprising an antibody or vaccine described herein.

Still another objective of the present invention is to provide a method of treating a subject (e.g., a human) who has, or is at risk for, a disorder characterized by aberrant accumulation of Aβ. Such a disorder can be a neurodegenerative disorder, such as AD or Down's syndrome. The method includes administering to the subject an antibody that specifically recognizes $A\beta_{N3pE-42}$. Optionally, the method can include evaluating the subject for a symptom of the disorder. For example, a patient with AD may be evaluated for one or more of: memory, language, praxis, attention, orientation to time or place, or other cognitive ability or symptom of dementia. The evaluation may be done before and/or after the administration. Such an evaluation is useful to determine the severity or stage of the disorder before and/or after treatment, for example, to determine the effect of the treatment on the subject. In a preferred embodiment, a pharmaceutical composition including an antibody described herein is administered in a therapeutically effective dose. The antibody can be administered alone or in combination with a second therapeutic agent, e.g., a cholinesterase inhibitor, vitamin E, hormone therapy, an antipsychotic agent, memantine, ampakine or a statin.

Also included is a method of treating a subject who has, or is at risk for, a disorder characterized by aberrant accumulation of Aβ, where the method includes administering to the subject a vaccine capable of inducing the production of antibodies that specifically recognize $A\beta_{N3pE-42}$.

The present inventors chose $A\beta_{N3pE-42}$ as a target to treat neurodegenerative diseases caused by the accumulation of Aβ. $A\beta_{N3pE-42}$ is found specifically in pathogenic brain lesions (e.g., AD plaques) but not in normal brain and other tissues. While not intending to be bound by theory, the inventors believe that specifically targeting $A\beta_{N3pE-42}$ in treatment of neurodegenerative diseases characterized by aberrant accumulation of Aβ (such as AD) may avoid the risk of unwanted immune complex formation in non-target tissues.

Because the amino acid sequence of $A\beta_{N3pE-42}$ differs from that of $A\beta_{42}$ by only the two amino acid residues at the N-terminus, it was presumed difficult to develop antibodies immunologically discriminating the two. The present inventors have now discovered that antibodies that specifically recognize $A\beta_{N3pE-42}$ can be produced. Such antibodies are useful in treating diseases characterized by aberrant accumulation of Aβ, such as neurodegenerative diseases caused by the accumulation of Aβ.

As used herein, the term "neurodegenerative disease caused by the accumulation of Aβ" means a disease comprising lesions of progressive neurodegeneration due to the accumulation of Aβ. Such diseases include Alzheimer's disease and Down's syndrome. Alzheimer's disease includes familial Alzheimer's disease, juvenile Alzheimer's disease and senile dementia of Alzheimer type.

As used herein, the term "a therapeutically effective amount" is an amount that produces a detectable improvement in one or more symptoms of the particular disease being treated. In preferred embodiments, the improvement is clinically significant. The effect of therapy can be evaluated by standard tests known to one of skill in the art. For example, the effect of a treatment on a patient with AD can be evaluated by a cognitive assessment test or brain imaging method.

DESCRIPTION OF THE PREFERRED EMBODIMENTS

Specifically, the present invention relates to antibodies, e.g., monoclonal antibodies, that specifically recognize $A\beta_{N3pE-42}$.

An antibody of the present invention may be prepared basically as stated below.

Monoclonal Antibodies

An antibody of the invention can be a monoclonal antibody. Such an antibody may be prepared, for example, by using $A\beta_{N3pE-42}$ or a peptide thereof, e.g., an N-terminal peptide, as antigen, immunizing an animal according to an ordinary immunization method, cell-fusing the immunized cells according to an ordinary cell fusion method, and cloning the fused cells according to an ordinary cloning method.

In particular, an antibody may be prepared by using $A\beta_{N3pE-42}$, or a peptide thereof, e.g., an N-terminal peptide, as the antigen, fusing spleen cells of a mammal immunized with the antigen with myeloma cells of a mammal such as a mouse, cloning the obtained fused cells (hybridomas), selecting clones producing antibody according to the present invention specifically recognizing $A\beta_{N3pE-42}$, and culturing them to recover the desired antibody. A synthetic antigen peptide of 6 residues (pEFRHDC; SEQ ID NO:4), comprising the first five N-terminal residues from the amino acid sequence of $A\beta_{N3pE-42}$ with a cys residue attached to its C-terminal end, which has been linked with a carrier protein via a crosslinking agent, is a preferred antigen to be used for the purpose of preparing monoclonal antibodies of the present invention. KLH (keyhole limpet hemocyanin) or the like can be used as the carrier protein. Such antigen proteins include, for example, pEFRHDC-MBS-KLH, which is shown herein in the Example. However, the method is only an example, and in this case, for example, not only the above pEFRHDC-MBS-KLH but also other domain peptides of $A\beta_{N3pE-42}$ having amino acid sequences comprising a N-terminal region thereof may be used as the antigens properly to prepare antibodies binding to $A\beta_{N3pE-42}$ specifically.

In the method of preparing such monoclonal antibodies, mammals to be immunized with the above antigen are not particularly restricted; it is preferable to select a mammal taking into account suitability with myeloma cells to be used in cell fusion, and preferably a mouse, a rat or a hamster is used.

Immunizations of the animal with the sensitizing antigen are performed in accordance with known methods. For example, as an example of a typical method, immunization can be performed by injecting the sensitizing antigen either intraperitoneally or subcutaneously. More specifically, after diluting and suspending the sensitizing antigen in a suitable amount of phosphate-buffered saline (PBS) or physiological saline, the resulting suspension is mixed with a suitable amount of an ordinary adjuvant, such as Freund's complete adjuvant, as necessary. Following emulsification, the resulting emulsion is suitable administered to the mammal over the course of several administrations every 4 to 21 days. In addition, a suitable carrier can be used during immunization with the sensitizing antigen.

After immunizing in this manner and confirming that the level of the desired antibody has risen in the serum, immune cells are removed from the mammal and used for cell fusion. Preferable examples of immune cells are spleen cells in particular. The myeloma cells of a mammal used as the other parent cells to be fused with above-mentioned immune cells can be any of various previously known cell strains, preferable examples of which include P3 (P3x63Ag8.653) (J. Immunol. 123: 1458, 1978), P3-UI (Current Topics in Microbiology and Immunology 81:1–7, 1978), NS-1 (Eur. J. Immunol. 6: 511–519, 1976), MPC-11 (Cell 8: 405–415, 1976), SP2/0 (Nature 276: 269–270, 1978), OF (J. Immunol. Meth. 35: 1–21, 1980), S194 (J. Exp. Med. 148: 313–323, 1978) and R210 (Nature, 277: 131–133, 1979).

Cell fusion of the above-mentioned immune cells and myeloma cells can be performed according to known methods, such as the method of Milstein, et al. (Millstein et al., Methods Enzymol. 73: 3–46, 1981). More specifically, the above-mentioned cell fusion is carried out during the course of ordinary nutrient culturing in the presence of a cell fusion promoter. Examples of fusion promoters that are used include polyethyleneglycol (PEG) and Sendai virus (HVJ). Moreover, an assistant such as dimethylsulfoxide can be added and used to improve fusion efficiency as desired.

The ratio of immune cells and myeloma cells used are preferably, for example, 1 to 10 times immune cells to myeloma cells. RPMI1640 culture medium and MEM culture medium suitable for growth of the above-mentioned myeloma cell strain as well as other ordinary culture medium used in this type of cell culturing can be used for the culture medium used for the above-mentioned cell fusion. Moreover, this can also be used in combination with serum supplements such as fetal calf serum (FCS).

For this cell fusion, the prescribed amounts of the above-mentioned immune cells and myeloma cells are mixed well in the above-mentioned culture medium followed by the addition of a PEG solution warmed in advance to about 37° C., for example a PEG solution having a mean molecular weight of about 1000 to 6000, normally at a concentration of 30 to 60% (w/v) and mixing to form the target fused cells (hybridoma). Continuing, by sequentially adding a suitable amount of culture medium and repeating centrifugation and removal of supernatant, cell fusion agents and so forth not suitable for hybridoma growth can be removed.

Said hybridoma is selected by culturing in an ordinary selective culture medium such as HAT culture medium (culture medium containing hypoxanthine, aminopterin and thymidine). Culturing in said HAT culture medium is usually contained for several days to several weeks or for an amount of time that is sufficient for eliminating all cells other than the target hybridoma (non-fused cells). Next, screening and single-cloning of hybridoma that produces the target antibody is performed by carrying out ordinary limiting dilution. A domain peptide including amino acid sequence of N-terminal of the $A\beta_{N3pE-42}$ is useful for the immunological screening of hybridoma. When the monoclonal antibodies of the present invention are selected by using the reactivity to the domain peptide as an index, it is advantageous to use the domain peptide that has been previously labeled. More specifically, first, the immunoglobulin molecules produced by the hybridomas are captured by an anti-immunoglobulin antibody. When screening is carried out for selecting the hybridomas of the present invention, it is convenient to use ELISA plates pre-coated with the anti-immunoglobulin antibody. The enzyme-labeled domain peptide is then allowed to react, and thus high-sensitivity screening can be performed for selecting hybridomas producing immunoglobulin having desired reaction specificity.

The monoclonal antibodies of the present invention specifically recognize $A\beta_{N3pE-42}$. In the present invention, when a monoclonal antibody has the ability of immunologically discriminating $A\beta_{N3pE-42}$ from $A\beta_{42}$ (e.g., because it binds $A\beta_{N3pE-42}$ with a higher affinity than $A\beta_{42}$) the antibody is said to specifically recognize $A\beta_{N3pE-42}$. A preferred monoclonal antibody of the invention recognizes $A\beta_{N3pE-42}$ but exhibits substantially no crossreactivity to other $A\beta_{42}$ species. For example, the antibody is reactive to $A\beta_{N3pE-42}$ but its reactivity to $A\beta_{42}$ under the same conditions is below the detectable level.

The present invention relates to hybridomas producing monoclonal antibodies specifically recognizing $A\beta_{N3pE-42}$. The hybridomas of the present invention are listed below:
hybridoma No. 16,
hybridoma No. 25,
hybridoma No. 22,
hybridoma No. 6,
hybridoma No. 5.

The splenic cells used in preparing these hybridomas were derived from mice immunized with particular antigens, as seen in the Example. Then, the hybridomas, which were provided by fusing the splenic cells and myeloma cells, were further screened by capturing with an anti mouse-IgG antibody and ELISA using POD-labeled antigens. The present inventors successfully prepared the hybridomas of the present invention by these procedures. Previously, there has been no monoclonal antibody specifically recognizing $A\beta_{N3pE-42}$.

A hybridoma producing a monoclonal antibody of the present invention is a novel fused cell prepared from a BALB/c mouse splenic cell and a mouse myeloma cell line P3X63Ag8.653 as parent cells, and was deposited on Apr. 2, 2002, under the name of 3pE-42 No. 16 (mouse—mouse hybridoma) with the accession number of FERM BP-7995, at International Patent Organism Depository in Japan, international depository authority according to Budapest Treaty on the International Recognition of the Deposit of Microorganisms for the purpose of patent procedures. The deposit of the 3PE-42 No. 16 mouse—mouse hybridoma (FERM BP-7995) will be maintained without restriction in the International Patent Organism Depository in Japan for a period of 30 years, or 5 years after the most recent request, or for the effective life of the patent, whichever is longer, and will be replaced if the deposit becomes non-viable during that period.

The hybridoma thus prepared that produces monoclonal antibody can be subcultured in ordinary culture medium, and stored for a long time in liquid nitrogen.

To prepare a monoclonal antibody from a hybridoma, the hybridoma is cultured in accordance with ordinary methods. The antibody can be prepared from the hybridoma culture supernatant, or the hybridoma can be transplanted into a mammal with which it is compatible, allowed to grow and then antibodies can obtained in the form of ascites. The former method is suitable for obtaining highly pure antibody, while the latter method is suitable for large-amount production of antibody.

In addition, monoclonal antibody is not only obtained from antibody-producing cells obtained by immunizing with antigen or from a hybridoma produced by cell fusion, but monoclonal antibody can also be used that is produced using gene recombination technology by cloning an antibody gene, incorporating that gene into a suitable vector, and introducing that vector into a known cell strain such as COS or CHO cells (see, for example, Vandamme et al., Eur. J. Biochem. 192:767–775, 1990).

Moreover, the monoclonal antibody obtained by using the above-mentioned methods can be purified to high purity by utilizing ordinary purification techniques such as salt precipitation, gel filtration or affinity chromatography. Monoclonal antibody produced in this manner can be confirmed to recognize antigen both at high sensitivity and high accuracy by ordinary immunological techniques such as radioimmunoassay (RIA), enzyme immunoassay (EIA, ELISA) and immunofluorescence analysis.

Modified Antibodies

Methods for making modified antibodies and antibody fragments are known in the art and can be found, e.g., in Zola, *Monoclonal Antibodies: Preparation and Use of Monoclonal Antibodies and Engineered Antibody Derivatives*. Springer Verlag (Dec. 15, 2000; 1st edition).

The antibody used in the present invention is not limited to a monoclonal antibody produced by a hybridoma, but may also be that which has been artificially modified, e.g., for the purpose of lowering heteroantigenicity to humans. For example, a chimeric antibody can be made that is composed of the variable regions of the monoclonal antibody of a mouse or other non-human mammal and constant regions of human antibody. This type of chimeric antibody can be produced using known methods for producing chimeric antibodies and particularly gene recombination technology.

Moreover, a reshaped human antibody can also be used in the present invention. A reshaped antibody is one in which the complementarity determining regions (CDR) of a human antibody are replaced with the complementarity determining regions of an antibody of a non-human mammal such as a mouse, and its general gene recombination techniques are known. A reshaped human antibody that is useful in the present invention can be obtained by using these known methods.

Furthermore, amino acids of the framework (FR) regions of the variable region of antibody may be substituted so as to form a suitable antigen binding site in the complementarity determining regions of the reshaped human antibody (Sato et al., Cancer Res. 53:1–6, 1933). A preferable example of this type of reshaped human antibody is humanized PM-1 (hPM-1) (see International Patent Application No. WO92-19759).

Moreover, a gene can be constructed that codes for antibody fragments, such as Fab or Fv, or a single chain Fv (scFv) in which Fv of the H chain and L chain are connected with a suitable linker. This gene can be expressed in a suitable host cell and used for the purpose described above, provided it binds to antigen and inhibits the activity of antigen (see, for example, Bird et al., TIBTECH 9:132–137, 1991; Huston et al., Proc. Natl. Acad. Sci. USA 85: 5879–5883, 1988). Moreover, the V region of the above-mentioned reshaped antibody can be used for the Fv of the H chain and L chain used for producing scFv.

In addition, the monoclonal antibody of the present invention can be a human antibody. The human antibody can be obtained by isolating cells producing the human antibody or cloning the human antibody gene isolated from the cells producing the human antibody. For example, there is a transgenic mouse line in which the original immune system has been replaced with the human immune system. An antibody that is obtained by immunizing such a mouse is a human antibody. In addition to this, the technologies of immortalizing and cloning human peripheral blood lymphocytes are known in the art. The human antibodies obtainable by these methods can be used in the present invention.

Thus, in one embodiment of the compositions and methods described herein, a monoclonal antibody described herein, e.g., a monoclonal antibody produced by hybridoma described herein, is modified to provide a chimeric, reshaped, or humanized antibody. In another embodiment, the LC and HC of a monoclonal antibody described herein, e.g., a monoclonal antibody produced by a hybridoma described herein, are cloned and/or their sequence determined in order to produce, by routine techniques, a biosynthetic antibody or fragment thereof, such as an Fab, DAB, Fv, or a single chain Fv (scFv) or the like.

An aspect of the invention provides methods of using the antibodies of the present invention, for treatment of neurodegenerative diseases caused by the accumulation of Aβ. A therapeutic method of the present invention comprises the step of administering an antibody, e.g., a monoclonal antibody, specifically recognizing $A\beta_{N3pE-42}$, to a patient. In the present invention, when human neurodegenerative diseases are to be treated, the preferred monoclonal antibody is a chimeric antibody with a human antibody molecule, reshaped human antibody or human antibody. The immunological reaction to the antibody molecule derived from a nonhuman species can be avoided by the use of these monoclonal antibodies. The host immune response to the administered antibody potentially reduces the effect provided by the administration. In addition, the immunological reaction should be prevented to secure the safety of the host as well.

A monoclonal antibody having at least the antigen-binding region is usable in the present invention. Since a monoclonal antibody further comprising the constant region enhances the removal of $A\beta_{N3pE-42}$ by the opsonin effect, such a monoclonal antibody can be a preferred antibody of the present invention. Antibody-bound $A\beta_{N3pE-42}$ is removed from brain tissues by phagocytes such as microglia.

Microglia are professional phagocytes and as such can provide beneficial functions by clearing targeted pathogens or cellular debris, and potentially, in AD the pathogenic peptide amyloid β(Aβ). In vivo: Schenk et al. showed that cerebral Aβ deposition in a transgenic mouse model that overexpress the gene for a mutant form of the human amyloid precursor protein (APP) was considerably diminished by prior immunization of the animals with synthetic Aβ peptide (Schenk et al., Nature 400:173–177, 1999). It has been reported that, in vitro, FCR-dependent ingestion of Aβ-anti-Aβ complexes (IgG-fAβ) by microglia that is a function of the amount of Ab used to form immune complexes (Webster et al., J. Immunol. 166:7496–7503, 2001).

Administration

The administration of an antibody to a patient can be initiated (a) when the subject begins to show symptoms of the disorder, e.g., when a subject beings to show symptoms of AD (such as dementia) as evidenced by art recognized diagnostic tests; (b) when a neurodegenerative disorder, such as AD, is diagnosed; (c) before, during or after another treatment for a neurodegenerative disorder, such as AD, is begun or begins to exert its effects; or (d) generally, as is needed to maintain health, e.g., cognitive function, throughout the natural aging process. The period over which the antibody is administered (or the period over which clinically effective levels are maintained in the subject) can be short term, e.g., for less than a year, six months, one month, two weeks or less; or long term, e.g., for six months or a year or more.

The route of administration and the amount of antibody delivered can be determined by factors that are well within the ability of skilled artisans to assess. Furthermore, skilled artisans are aware that the route of administration and dosage of a therapeutic antibody may be varied for a given patient until a therapeutic dosage level is obtained.

When an agent is used for brain tissues, delivering the agent to brain tissues represents the greatest challenge. The brain is a tissue that is protected with the blood brain barrier (BBB). The BBB prevents the brain from coming into contact with various substances. The protective mechanism of the BBB is assumed to include inhibiting the permeation of substances and eliminating substances from the brain. Namely, in therapy for brain tissue, it is important to allow the agent to stay in the brain as well as to permeate across the BBB.

In the present invention, an antibody, e.g., a monoclonal antibody, is administered. Thus, it is necessary for the antibody to enter the brain and immunologically react to $A\beta_{N3pE-42}$. The antibody molecule is a biological molecule and therefore can permeate across the BBB.

The antibody delivery through blood-brain barrier and cellular enhancement of cellular uptake of antibodies by cationic modification has been documented in animal studies (Partridge, Trends Biotechnol, 12:239–245, 1994).

Further, the monoclonal antibody can be linked with a BBB-permeable carrier to improve the permeability across the BBB. As used herein, the term "BBB-permeable carrier" means a substance capable of delivering an antibody or the antigen-binding region through the BBB into the brain. For example, the following carriers can be used in the present invention.

Pegelin and Penetratin
Receptor-mediated transcytosis systems that mediate the
    BBB transport of circulating endogenous large molecular peptides, such as insulin or transferrin
    Anti-transferrin receptor monoclonal antibody
    Insulin receptor monoclonal antibody Pegelin and penetratin are proteins that exhibit anti-microbial activity, perforating the cell membrane, which are derived from the small U-shaped protegrin. There are two types of molecules previously reported, namely dox-D-penetratin consisting of 16 amino acid residues (RQIKIW-FQNRRMKWKK; SEQ ID NO:2) and dox-SynB1 consisting of 18 amino acid residues (RGGRLSYSRRRFSTSTGR; SEQ ID NO:3). The antibody, which has been coupled with either of the two types of molecules via a linker, can be delivered into the brain by peripheral administration (Temsamani et al., Current Trends, 3:155–158, 2000). The system of drug delivery into the brain using these peptides is called "Pep:trans technology" and is being studied for practical use by Synt:em. Alternatively, such heterologous sequence may be fused with the monoclonal antibody of the present invention. Accordingly, in a preferred embodiment, the present invention provides a fusion protein comprising sequence heterologous to the monoclonal antibody.

Alternatively, an anti-transferrin receptor (TfR) monoclonal antibody can be linked with a substance and used as a carrier for delivering the substance into the brain, because TfR is present in the BBB. The coupling of an antibody and BBB transporter vector as the carrier can be achieved by a conjugation method with avidin-biotin technology, pegylation technology using a polyethylene glycol (PEG) linker or liposome technology (Kurihara and Pardridge, Canc Res 54: 6159–6163, 1999; Pardridge, Bioscience, 52:577–583, 2001).

For example, it has been known that the brain-derived neurotrophic factor (BDNF) hardly enter the brain by intravenous administration but PEGylated BDNF or the homodimer conjugated with an anti-TfR monoclonal antibody by biotin-streptavidin technology can passage through the BBB and enter the brain. 2000-Da polyethylene glycol was used as polyethylene glycol (Zhang and Partridge, Brain Res 889: 49–56, 2001).

In the present invention, the antibody recognizing $A\beta_{N3pE-42}$ can be conjugated with the anti-TfR receptor antibody as the carrier to improve the BBB permeability.

Furthermore, the monoclonal antibody can be given efficiently to brain tissues when DNA encoding a peptide containing the antigen-binding region of the antibody is expressed in the brain tissue. The protein of interest can be expressed in brain tissues by inserting a DNA of interest into an appropriate vector encompassing a promoter for nervous tissue-specific expression and introducing the vector into brain cortex and hippocampal tissue by a targeting method. Such vectors to be used include, for example, viral vector and plasmid DNA. Plasmid DNA is a preferred vector of the present invention for the following reasons:

ensures the stable expression of proteins in neurons,
    is not integrated into the host chromosome, and
    does not direct the expression of viral proteins, and thus there is no possibility that it is recognized as foreign material and is eliminated or exhibits toxicity.

The following vectors can also be used: herpesvirus vector, poliovirus vector, adenovirus vector, adeno-associated virus vector, and CAG (Plasmid DNA). "CAG" means a vector comprising the cytomegalovirus enhancer, chicken β-actin promoter and rabbit β-globin polyA signal.

According to a known method, an expression vector can be constructed by inserting a gene of interest into any of the vectors. Further, the expression vector can also be targeted to brain cortex or hippocampal tissue according to known methods. For example, plasmid DNA which has been encapsulated in liposome, can be delivered into the brain. In this report, polyethyleneglycol and an anti-TfR monoclonal antibody were linked to liposome. This expression vector was peripherally administered; the exogenous DNA integrated in DNA was expressed in the brain tissue (Shi et al., Pharm. Res. 18: 1091–1095, 2001).

The pharmaceutical composition of the present invention is preferably administered parenterally, and can be administered systemically or topically by, for example, intravenous injection, intramuscular injection, intraperitoneal injection or subcutaneous injection. Moreover, it can also take on the form of a pharmaceutical composition or kit with at least one type of pharmaceutical vehicle or diluent, preferably a sterile pharmaceutical vehicle or diluent.

Although varying according to patient condition and age or by the method of administration, it is necessary to select a suitable dose for the dose of the pharmaceutical composition of the present invention for human. For example, a dose divided among four administrations or less within the range of about 1 to 1000 mg/patient can be selected. In addition, it can be administered at a dose of 1 to 10 mg/kg/week. However, the pharmaceutical composition of the present invention is not limited to these doses.

The pharmaceutical composition of the present invention can be prepared in accordance with routine methods. For example, to prepare an injection preparation, purified $A\beta_{N3pE-42}$ antibody or antigen binding region thereof is dissolved in a solvent such as physiological saline or buffer, followed by the addition of an adsorption preventive such as Tween80, gelatin or human serum albumin (HSA). Alternatively, it may also be freeze-dried in order to be reconstituted prior to use. Examples of vehicles that can be used for freeze-drying include sugar alcohols and sugars such as mannitol and glucose.

Vaccines

The present invention also includes a vaccine composition for inducing a antibody that specifically recognizes $A\beta_{N3pE-42}$ in a host. A vaccine preparation of the present invention contains an antigen that is capable of inducing the production of antibodies specifically recognizing $A\beta_{N3pE-42}$ in the host. Preferred antigens in the present invention include, for example, a similar protein or domain peptide as the antigen used to prepare the above-mentioned monoclonal antibodies. Such peptides include peptides not present in $Ab_{42}$ and $Ab_{40}$. A preferred peptide for vaccination is a peptide derived from the N-terminus of $A\beta_{N3pE-42}$, e.g., EFRHDC (SEQ ID NO:5).

Routine methods exist for formulating vaccine preparations from such antigens. For example, the antigen and suitable adjuvant are dissolved in a solvent such as physiological saline or buffer, followed by the addition of an adsorption preventive such as Tween80, gelatin or human serum albumin (HSA). Alternatively, it may also be freeze-dried in order to be reconstituted prior to use. Examples of vehicles that can be used for freeze-drying include sugar alcohols and sugars such as mannitol and glucose.

Techniques for making and optimizing vaccines are known in the art. For example, detailed guidance can be found in *Vaccine Protocols*. Robinson, Farrar and Wiblin (Editors), Humana Press (Aug. 15, 1996); and *New Vaccine Technologies* Ronald W. Ellis (Editor) Landes Bioscience (Jun. 1, 2001).

The disclosures of all the above-identified reference publications are herein incorporated and made part of this disclosure.

Although the following provides a detailed explanation of the present invention through its reference examples and examples, the present invention is not limited to them.

EXAMPLES

Example 1

Antibody Preparation

This example describes the production of monoclonal antibodies that specifically recognize $A\beta_{3pE-42}$.

1. Antigen

A synthetic antigen peptide of 6 residues (pEFRHDC; SEQ ID NO:4), comprising the first five N-terminal residues from the amino acid sequence of $A\beta_{3pE-42}$ with a cys residue attached to its C-terminal end, was linked with the carrier protein KLH (keyhole limpet hemocyanin) via the crosslinking agent MBS (m-maleimidobenzoyl-N-hydroxysuccinimide) (hereinafter referred to as "pEFRHDC-MBS-KLH"). This conjugated entity was used as the antigen.

2. Immunization

A pEFRHDC-MBS-KLH solution was mixed with Freund's complete adjuvant at a ratio of 1:1. An emulsion was prepared from the mixture and given twice to mice (BALB/c; female; approx. 6 weeks old). The second injection was carried out about 3 weeks after the first one. The antigen was given by subcutaneous injection at several sites on the back. The dose of pEFRHDC-MBS-KLH given to a mouse was about 100 µg. At the final immunization, about 150 µg of pEFRHDC-MBS-KLH, which had been diluted with physiological saline, was given to the peritoneal cavity.

The splenic cells were prepared as follows. 3 days after the final immunization, the spleens were resected from the mice, and crushed with a frosted glass device to disperse the splenic cells in RPMI-1640 medium (GIBCO). The dispersion was filtered to remove tissue debris. Then, erythrocytes were lysed with a RBC Lysing Buffer (Sigma). The cells were centrifuged and then washed once with RPMI-1640 medium. The cells were used in the cell fusion experiment.

Mouse myeloma cells (P3X63Ag8.653 line) were grown in a GIT medium (Wako Pure Chemical Industries, Ltd) containing 0.5% BriClone (DAINIPPON PHARMACEUTICAL) and 50 µg/mL gentamicin sulfate (Schering-Plough) at 37° C. under 5% $CO_2$. The cells were centrifuged and then washed once with an RPMI-1640 medium. The cells were used in the cell fusion experiment.

3. Cell Fusion

Cell fusion was carried out as follows. The splenic cells and mouse myeloma cells were mixed at a ratio of 10:1, and then centrifuged. The supernatant was discarded. An RPMI-1640 medium containing 50% polyethylene glycol was added to the cells. The mixture was vigorously stirred for 1 minute at room temperature, and then allowed to stand for 1 minute. 25 times as much volume of RPMI-1640 was added to stop cell fusion. The cells were centrifuged, and then suspended in a HAT medium (GIT medium containing 10% fetal calf serum (Hyclone; hereinafter abbreviated as "FCS"), 0.5% BriClone, 100 µM hypoxanthine, 0.4 µM aminopterin, 16 µM thymidine, and 50 µg/mL gentamicin sulfate). 100 µl aliquots of the suspension, which comprise $4 \times 10^5$ cells, were added to the wells of 96-well microplates. The plates were incubated at 37° C. under 5% $CO_2$ for hybridoma selection.

50 µl of HAT medium was added twice to the wells. The interval between the first and second addition was 3–4 days. Finally, the medium was changed to a fresh HAT medium. After 2–3 days, if growth of the hybridomas was detected, the culture supernatants were collected and the screening was carried out by using the supernatants.

4. Screening for Anti-$A\beta_{3pE-5}$ Antibody-Producing Hybridomas

The screening for anti-$A\beta_{3pE-5}$ antibody-producing hybridomas was carried out as follows.

An affinity-purified rabbit anti-mouse IgG (Fc) antibody (Rockland) was diluted with 50 mM carbonate buffer (pH 9.6), and 50 µL aliquots were added to the respective wells of 96-well flat-bottomed ELISA plates (NUNC). The plates were allowed to stand at 4° C. overnight. Then, the supernatants were discarded, and the respective wells were filled with a 25% BlockAce solution (Snow Brand) for blocking. The plates were allowed to stand at 4° C. overnight or longer. The plates were stored under this condition until they were used.

A synthetic antigen peptide of 6 residues (pEFRHDC, SEQ ID NO 4) was linked with peroxidase (Toyobo; hereinafter abbreviated as POD) via the crosslinking agent GMBS (N-succinimidyl 4-maleimidobutyrate) (DOJINDO), which was used as the labeled antigen (pEFRHDC-GMBS-POD).

ELISA was carried out as described below. A 50 µL aliquot of the supernatant of hybridoma culture was added to each well of a plate on which an affinity-purified rabbit anti-mouse IgG (Fc) antibody has been immobilized; the plate was allowed to stand at room temperature for one hour. The plate was washed 10 times with a washing solution (phosphate buffer saline (hereinafter abbreviated as PBS) containing 0.05% Tween 20) and 50 µL-aliquots of a solution of labeled antigen adequately diluted with PBS solution containing 10% BlockAce were added to the respective wells. The plate was allowed to stand at room temperature for one hour. The plate was washed 10 times with the washing solution, and then 50 µL-aliquots of a solution of TMB reagent (Funakoshi) were added to the respective wells. The plate was allowed to stand for 15 minutes. Finally, 1 M phosphoric acid or 2 M sulfuric acid was added to the plate to stop the enzyme reaction. Absorbance of each well was determined at 450 nm in a microplate reader. The wells with higher absorbance were selected, and the cells corresponding to the wells were collected. The cells were grown in an HT medium (GIT medium containing 10% FCS, 0.5% BriClone, 100 μM hypoxanthine, 16 μM thymidine and 50 μg/mL gentamicin sulfate) at 37° C. under 5% $CO_2$. The cells were subjected to cloning.

5. Hybridoma Cloning

Hybridoma cloning was carried out by the soft agar method. 9 times as much volume of an HT medium was added to an autoclaved 2.5% Bacto-agar (DIFCO); the mixture was mixed well and kept at 37° C. The hybridomas were adequately diluted with this solution; a 3 mL aliquot was transferred to a dish (Falcon). The dish was cooled at 4° C. for 30 minutes, and then incubated at 37° C. under 5% $CO_2$ for 7–10 days. When colonies were found on soft agar, colonies were picked with 1 ml syringes (Terumo) under a microscope. Then, the cells were grown in the HT medium in 24-well cell-culture microplates (NUNC). After 2–3 days, if the growth was recognized, the culture supernatants were collected and the screening was performed with the supernatants. This step was repeated one more time, and finally, single-clone hybridoma lines were established.

6. Specificity of Antibody

Each of solutions of $A\beta_{N3pE-42}$, $A\beta_{N3E-42}$ and $A\beta_{1-40}$ in DMSO was diluted with 50 mM carbonate buffer (pH 9.6); the final concentration of each Aβ was 1 μg/mL. 50 μL-aliquots of the solutions were added to the wells of 96-well flat-bottomed ELISA plates (NUNC); the plates were allowed to stand at 4° C. overnight. The plates were washed 2 or 3 times with distilled water, and then the respective wells were filled with 25% BlockAce solution. The plates were allowed to stand at 4° C. overnight or longer. The plates were stored under this condition until they were used. At the time of use, the solution in each well was completely discarded.

The culture supernatants of hybridoma clones (No. 16, No. 25, No. 22, No. 6, and No. 5) obtained in this experiment and culture supernatants of hybridomas producing no anti-Aβ antibody as negative controls were combined with a 10% BlockAce solution at a ratio of 1:1, and the mixtures were used as the samples. Another sample was prepared as a positive control by diluting 1000 times a solution of the monoclonal antibody mAb4G8 (SENETEC Inc) whose epitope is Aβ 17–28 with 10% BlockAce solution. 50 μL aliquots of these samples were added to plates on which the above-mentioned Aβ peptides were immobilized, and then plates were allowed to stand at room temperature for about one hour. The plates were washed 5 times with a washing solution (PBS containing 0.05% Tween 20) and then 50 μL aliquots of a horseradish peroxidase-conjugated goat anti-mouse Igs antibody (CAPPEL) diluted 2000 times with 10% BlockAce solution were added thereto. The plates were allowed to stand at room temperature for about 30 minutes, and then washed 5 times with the washing solution. 50 μL-aliquots of a solution of TMB reagent were added to the plates. The plates were allowed to stand at room temperature for 15 minutes. Finally, 50 μL aliquots of a solution of 1 M phosphoric acid were added to the plates to stop the enzyme reaction. The absorbance was determined at 450 nm in a microplate reader.

7. Experimental Results

The results obtained with the antibodies are shown in Table 1. In all the positive controls, Aβ peptides gave 1.0 or higher absorbance values, and thus it was confirmed that enough amounts of the Aβ peptides were immobilized. In all negative controls, Aβ peptides gave 0.1 or lower absorbance values, and thus it was confirmed that the level of non-specific reaction was very low. In the culture supernatants of the five hybridoma clones obtained in this experiment, only the absorbance of $A\beta_{N3pE-42}$ was as high as that of the positive controls. On the other hand, the absorbance of $A\beta_{3E-42}$ and $A\beta_{1-40}$ was as low as that of the negative controls. Based on the result described above, the present inventors reached a conclusion that all the hybridoma clones obtained in this experiment produce antibodies highly specifically recognizing the N-terminus of $A\beta_{N3pE-42}$.

TABLE 1

Specificity of antibodies produced by the hybridomas

| Sample | $A\beta_{N3pE-42}$ | $A\beta_{1-40}$ | $A\beta_{N3E-42}$ |
|---|---|---|---|
| Hybridoma No. 16 | 2.40 | 0.02 | 0.02 |
| Hybridoma No. 25 | 2.35 | 0.03 | 0.03 |
| Hybridoma No. 22 | 1.55 | 0.03 | 0.10 |
| Hybridoma No. 6 | 2.21 | 0.02 | 0.02 |
| Hybridoma No. 5 | 2.34 | 0.02 | 0.02 |
| Negative control | 0.02 | 0.02 | 0.02 |
| Positive control | 2.27 | 1.57 | 1.39 |

Example 2

Functional Evaluation of Anti-$A\beta_{N3pE-42}$ Antibodies

This example describes the functional evaluation of anti-$A\beta_{N3pE-42}$ antibodies.

The applicability of anti-$A\beta_{N3pE-42}$ monoclonal antibodies to therapeutics for Alzheimer's disease is tested by analyzing the antigen-antibody reaction detected after addition of anti-$A\beta_{N3pE-42}$ monoclonal antibodies and the subsequent physiological response mainly using an in vitro model of amyloid deposition in senile plaque.

Evaluation of in Vitro Model

The evaluation is performed with the in vitro senile plaque model using synthetic Aβ reported by Isobe et al. (National Institute for Longevity Sciences) (Isobe et al., Exp Neurol. 162: 51–60, 2000); artificial senile plaques prepared with the synthetic $A\beta_{1-40}$, $A\beta_{1-42}$ or $A\beta_{3pE-42}$ are added to the primary culture of glial cells or mixed brain cell primary culture and the subsequent changes in the various culture cells are studied histologically or biochemically. Then, the anti-$A\beta_{N3pE-42}$ monoclonal antibodies are added in this experimental system. The presence of binding between each antibody and Aβ is tested and the induced changes in phagocytosis by microglial cells and astrocyte aggregation are compared with those induced by polyclonal antibodies or other anti-$A\beta_{1-5}$, anti-$A\beta_{1-25}$ antibodies or the like. Further, with this experimental system, a system for quantifying senile plaque (Aβ) is developed and then quantitative changes in senile plaque (Aβ) are determined in the presence and absence of the antibodies.

The antibodies, e.g., monoclonal antibodies, of the present invention are useful for treating and diagnosing neurodegenerative diseases including Alzheimer's disease. For example, pharmaceutical compositions comprising the antibodies of the invention can be administered to a patient with a disease associated with the accumulation of $A\beta_{N3pE-42}$ to treat the patient. It has already been confirmed that administration of an antibody recognizing $A\beta_{42}$ gives a therapeutic effect on neurodegenerative diseases. However, $A\beta_{42}$ is also a protein present in blood, and thus, if the antibody recognizing $A\beta_{42}$ is administered, there is a risk of side effect by the immune complex formed.

On the other hand, the monoclonal antibodies to be used in the present invention are those specifically recognizing $A\beta_{N3pE-42}$. Because $A\beta_{N3pE-42}$ is localized in brain lesions in neurodegenerative diseases, there is no risk of side effect by the immune complex. Thus, safer pharmaceutical compositions can be provided by using the monoclonal antibodies of the present invention.

Furthermore, the antibodies of the present invention are useful in diagnosing diseases associated with the accumulation of $A\beta_{N3pE-42}$. For example, antibodies of the present invention can be applied to imaging technology for examining lesions that are recognized with an antibody by monitoring the localization of the antibody. The antibodies of the present invention specifically accumulate in the lesions, and thus can provide images with great S/N ratios. On the other hand, since $A\beta_{42}$ is a protein present in blood, it is not expected that an antibody recognizing $A\beta_{42}$ will provide high enough contrast in the imaging.

What is claimed is:

1. A hybridoma cell line deposited under accession number of FERM BP-7995, at International Patent Organism Depository in Japan.

2. A monoclonal antibody produced by the hybridoma of claim 1, or the antigen-binding region thereof.

3. A polypeptide comprising the antigen binding region of the monoclonal antibody of claim 2.

4. The polypeptide of claim 3, wherein the polypeptide is a single chain antibody.

5. The polypeptide of claim 3, wherein the polypeptide is a humanized antibody.

6. The polypeptide of claim 3, wherein the polypeptide is an Fab', Fab, F(ab')2, Fv or scFv.

7. The polypeptide of claim 3, wherein the polypeptide is a fusion protein comprising sequence heterologous to the monoclonal antibody.

* * * * *

SEQUENCE LISTING

```
<160> NUMBER OF SEQ ID NOS: 5

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 16
<212> TYPE: PRT
<213> ORGANISM: Homo sapiens

<400> SEQUENCE: 2

Arg Gln Ile Lys Ile Trp Phe Gln Asn Arg Arg Met Lys Trp Lys Lys
 1               5                  10                  15

<210> SEQ ID NO 3
<211> LENGTH: 18
<212> TYPE: PRT
<213> ORGANISM: Homo sapiens

<400> SEQUENCE: 3

Arg Gly Gly Arg Leu Ser Tyr Ser Arg Arg Arg Phe Ser Thr Ser Thr
 1               5                  10                  15

Gly Arg

<210> SEQ ID NO 4
<211> LENGTH: 6
<212> TYPE: PRT
<213> ORGANISM: Artificial Sequence
<220> FEATURE:
<221> NAME/KEY: PHOSPHORYLATION
<222> LOCATION: 1
<220> FEATURE:
<223> OTHER INFORMATION: Synthetically generated peptide

<400> SEQUENCE: 4

Glu Phe Arg His Asp Cys
 1               5

<210> SEQ ID NO 5
<211> LENGTH: 6
<212> TYPE: PRT
<213> ORGANISM: Artificial Sequence
<220> FEATURE:
```

-continued

```
<223> OTHER INFORMATION: Syntheticaly generated peptide

<400> SEQUENCE: 5

Glu Phe Arg His Asp Cys
 1               5
```